(12) United States Patent
Pickett et al.

(10) Patent No.: US 8,908,164 B2
(45) Date of Patent: Dec. 9, 2014

(54) METHOD FOR THE DETECTION OF DEFECTS IN GAS-BARRIER FILMS USING QUANTUM DOTS

(71) Applicant: Nanoco Technologies, Ltd., Manchester (GB)

(72) Inventors: Nigel Pickett, Manchester (GB); Nathalie Gresty, Chester (GB)

(73) Assignee: Nanoco Technologies, Ltd. (GB)

(*) Notice: Subject to any disclaimer, the term of this patent is extended or adjusted under 35 U.S.C. 154(b) by 0 days.

(21) Appl. No.: 13/887,090

(22) Filed: May 3, 2013

(65) Prior Publication Data
US 2013/0314698 A1 Nov. 28, 2013

Related U.S. Application Data

(60) Provisional application No. 61/642,934, filed on May 4, 2012.

(51) Int. Cl.
*G01N 21/64* (2006.01)
*G01N 21/59* (2006.01)
*G01N 21/91* (2006.01)
*G01N 21/84* (2006.01)
*G01N 15/08* (2006.01)

(52) U.S. Cl.
CPC .............. *G01N 21/64* (2013.01); *G01N 21/59* (2013.01); *G01N 21/91* (2013.01); *G01N 21/6489* (2013.01); *G01N 2021/8427* (2013.01); *G01N 2015/0813* (2013.01)
USPC ...................................................... 356/72

(58) Field of Classification Search
CPC . G01N 2021/646; G01N 21/59; G01N 21/64; G01N 15/08; G01N 21/6489; G01N 21/6428; G01N 33/588; G01N 33/582; G01N 21/91; B82Y 20/00; B82Y 15/00; B82Y 40/00; B82Y 99/00; H01L 33/06; H01L 29/127; H01S 5/3412; H01S 5/341; H01S 3/169; H01S 5/34

USPC .......... 356/432, 72, 317; 250/459.1; 977/774, 977/773, 950, 834, 949, 824, 815
See application file for complete search history.

(56) References Cited

U.S. PATENT DOCUMENTS

| | | | |
|---|---|---|---|
| 2004/0036130 A1* | 2/2004 | Lee et al. | 257/409 |
| 2010/0291685 A1 | 11/2010 | Zhang | |
| 2011/0163291 A1* | 7/2011 | Scarsbrook et al. | 257/9 |
| 2012/0199952 A1* | 8/2012 | D'Evelyn et al. | 257/615 |
| 2014/0022779 A1* | 1/2014 | Su et al. | 362/231 |

FOREIGN PATENT DOCUMENTS

| | | |
|---|---|---|
| EP | 2003439 A1 | 12/2008 |
| JP | 2010269302 A * | 12/2010 |

OTHER PUBLICATIONS

"Potential Clinical Applications of Quantum Dots" to Medintz et al., Int. J. of Nanomedicine 2008: 3(2) 151-167.*

(Continued)

*Primary Examiner* — Tarifur Chowdhury
*Assistant Examiner* — Mohamed Amara
(74) *Attorney, Agent, or Firm* — Wong, Cabello, Lutsch, Rutherford & Brucculeri LLP.

(57) ABSTRACT

By forming nanoparticles from gas-phase precursors within cracks or defects in a gas-barrier film, crack-width may be determined from the diameter of the nanoparticles formed within. The optical absorption and emission wavelengths of a quantum dot are governed by the particle size. For a particular material, the absorption and/or emission wavelengths may therefore be correlated to the particle size (as determined from techniques such as transmission electron microscopy, TEM). Thus, fluorescence measurement techniques and/or confocal microscopy may be used to determine the size of quantum dots formed within a gas-barrier film, allowing both the size and nature of a defect to be determined. The method may be used to assess the potential effects of defects on the integrity of the gas-barrier film.

21 Claims, 7 Drawing Sheets

(56) References Cited

OTHER PUBLICATIONS

Williams W B et al. "Using Quantum Dots to Tag Subsurface Damage in Lapped and Polished Glass Samples" Applied Optics, Optical Society of America, Washington, DC; US, vol. 48, No. 27, Sep. 20, 2009, pp. 5155-5163.

International Search Report dated Sep. 11, 2013.

* cited by examiner

METHOD FOR THE DETECTION OF DEFECTS IN GAS-BARRIER FILMS USING QUANTUM DOTS

RELATED APPLICATIONS

This application claims the benefit of U.S. Provisional Application No. 61/642,934, filed May 4, 2012, the entire contents of which are hereby incorporated herein by reference.

BACKGROUND

This invention relates to thin film gas-barriers. More particularly, it relates to methods for characterizing thin film gas-barriers using gas-phase synthesis of quantum dots.

In the electronics industry, much work has been carried out into the development of effective gas-barriers for electronic devices. Gases such as $O_2$ and water vapor can detrimentally affect the stability and performance of electronic devices. Therefore a gas-barrier film may be applied on top of the active device layer to shield the active layer from such contaminants. In addition, gas-barrier films may impart functionality, such as flexibility or shock-resistance, to electronic devices.

Gas-barrier films are employed in other areas in addition to the electronics industry. For example, in the packaging industry gas-barrier films are used to protect foods and pharmaceuticals from bacteria and other contaminants.

Typical gas-barriers are organic, inorganic, or inorganic-organic hybrid materials. Examples of organic materials include polymers (acrylates, epoxides, polyamides, polyimides, polyesters, cellulose derivatives, etc.), which are often hydrophobic in nature. Inorganic gas-barriers may include dielectric (insulating) materials, metal oxides, metal nitrides, or silica-based (glass) materials. For inorganic-organic hybrids, the organic component is often a polymer, e.g. a silica-acrylate hybrid.

Figure 1:
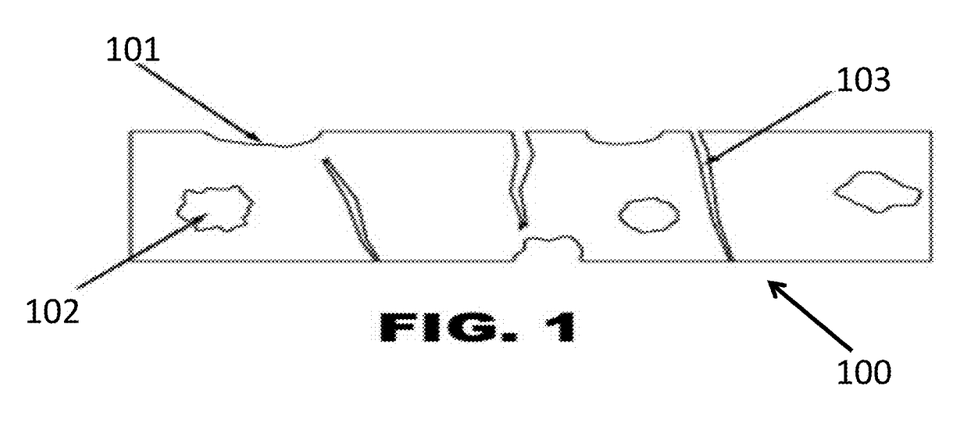
FIG. 1 is an illustration of defects in a gas-barrier film.

For a gas-barrier film to function effectively, it must be impenetrable to small molecules. Therefore, any cracks or channels in the film must be eliminated. Some examples of potential defects in a thin film are illustrated in FIG. 1. Such defects in a film 100 include open pores 101, pinholes/closed pores 102 and cracks 103. Closed pores are inaccessible to small molecules and therefore do not compromise the film integrity. However, such pores are still undesirable as they may weaken the film. Full-thickness cracks compromise the film integrity by allowing gas molecules to diffuse through, potentially reducing the device stability and performance. Defects in contact with just one surface of a film are also undesirable since they have the potential to propagate to full-thickness cracks.

As such, it is necessary to have a non-destructive method to detect defects in gas-barrier films. It is also advantageous to have a testing method that tests the gas-barrier's penetrability to gases. In addition, a detection technique that may characterize the defect structure of a film, rather than just defect pore size distribution, is highly desirable.

Methods of the prior art used to detect defects in films include mercury intrusion porosimetry, and nitrogen gas adsorption. Mercury intrusion porosimetry is a method used to characterize pores in solid films, particularly in the packaging in the pharmaceutical industry. Using low-pressure mercury, pore diameters between 14-200 μm may be detected, while high pressure mercury porosimetry may be used to detect pore diameters down to 3 nm. The technique was first developed by Ritter and Drake in the 1940s [H. L. Ritter & L. C. Drake, *Ind. Eng. Chem. Anal. Ed.*, 1945, 17, 782]. The technique exploits the dependence of the rate of penetration of a liquid into a medium on the size and distribution of pores within the medium. Elemental mercury is ideally suited to this technique since it is non-wetting to most solids. The pressure required to force a non-wetting liquid into a capillary of circular cross-sectional area is inversely proportional to the capillary diameter and is directly proportional to both the surface tension of the liquid and the contact angle made with the solid surface. Therefore, for a given applied pressure it is possible to calculate the size of the pores that Hg will enter and those it will not.

However, the 3 nm lower detection limit of mercury intrusion porosimetry is inadequate for verification of the integrity of gas-barrier films, since molecules of water and oxygen are an order of magnitude smaller and may diffuse through much narrower cracks. Further, mercury intrusion porosimetry may be used to give an indication of defect diameter, but does not provide any visual representation of the defect structure. The model assumes a cylindrical pore shape, which is not always accurate. Using conventional apparatus, the detection area is also limited to approximately 1 $cm^2$, so larger films cannot be characterized by this technique. The technique relies upon high operating pressures, which may be damaging to the film or electronic device. These high pressures may be particularly detrimental when a sample contains many closed pores, which cannot be detected using this technique, as the high pressures may compress a sample. Mercury intrusion porosimetry has also been found to overestimate the diameter of very small pores.

Gas adsorption porosimitry may be used to determine the pore size distribution of a material from its gas adsorption isotherm [C. G. Shull, *J. Am. Chem. Soc.*, 1948, 70, 1405]. Nitrogen gas adsorption is used in the detection of pores with a wide range of diameters from 3 Å to 300 nm. The technique may be used to determine pore volumes, along with the volume pore size distribution, based on a similar technique to mercury intrusion porosimetry, except replacing the non-wetting liquid with nitrogen gas. In the pore size range where capillary condensation occurs, capillary condensation into pores for a condensate with a concave meniscus will ensue provided the pressure of the adsorbate exceeds the equilibrium pressure of liquid in the pore. The pore size distribution may be determined from the adsorption or desorption isotherm.

As with mercury adsorption porosimetry, the nitrogen gas adsorption technique assumes a cylindrical pore shape, with open pores, and an absence of pore networks. Therefore, it may be inaccurate in characterizing the pore distribution in systems wherein the pore structure deviates from these criteria. In addition, the acquisition of a single measurement may take several hours. Other drawbacks include the fact that the sample may come into contact with liquid nitrogen during the course of the measurement, which may result in damage to the sample, and cryogenic temperatures are required to ensure little attraction between the gas-phase molecules, which may be difficult and costly to maintain.

BRIEF SUMMARY

A method of synthesizing quantum dots (QDs) using gaseous precursors within defects in gas-barrier films is disclosed herein. A gas barrier film is exposed to gas-phase quantum dot precursors. The gas-phase precursors can diffuse into any pores that are present in the film and react within those pores to form QDs.

The disclosed method takes advantage of the fact that QDs emit light upon stimulation and that the wavelength of the emitted light is a function of the diameter of the QDs. Thus, pores containing QDs can be visualized by observing the emission from the QDs. Moreover, the wavelength of the emission provides an indication of the size of the pore because it will be known that the pore is at least large enough to contain a QD generating the observed wavelength of emission.

The method may be used to detect defects that are in some way connected to the film surface(s), e.g. channel cracks, open pores/pinholes and pinholes connected to cracks. The technique is not restricted to any specific defect geometry. The optical properties of the quantum dots may be used to determine the particle size and thus the dimensions and nature of the defects within the film.

DETAILED DESCRIPTION

Quantum dots (QDs) are small particles, i.e., "nanoparticles", of a semiconductor material. Well-known QDs are nanoparticles of chalcogenides (selenides or sulfides) of metals such as cadmium or zinc (CdSe or ZnS, for example). QDs typically range from 2 to 10 nanometers in diameter (about the width of 50 atoms), but may be larger, for example up to about 100 nanometers.

Because of their small size, quantum dots display unique optical and electrical properties that are different in character to those of the corresponding bulk material. The most immediately apparent of these optical properties is the emission of photons under excitation. The wavelength of these photon emissions depends on the size of the quantum dot.

The ability to precisely control the size of a quantum dot enables the manufacturer to determine the wavelength of its emission, which in turn determines the color of light the human eye perceives. Quantum dots may therefore be "tuned" during production to emit any color of light desired. The ability to control, or "tune" the emission from the quantum dot by changing its core size is called the "size quantization effect".

The smaller the QD, the higher the energy, i.e., the more "blue" its emission is. Likewise, larger QDs emit light more toward the red end of the spectrum. Dots may even be tuned beyond visible light, into the infra-red or into the ultra-violet portions of the electromagnetic spectrum.

Once synthesized, quantum dots are either a powder or in a solution. Because of their tiny size, the ability to produce even a relatively "small" volume of quantum dots (e.g. one kilo) will yield enough actual quantum dots for industrial scale applications.

Gas-phase synthesis of nanoparticles has been described in the prior art by Pickett et al. [N. L. Pickett et al., *J. Mater. Chem.*, 1997, 7, 1855; *J. Mater. Chem.*, 1996, 6, 507]. The size of the resultant quantum dots may be varied by careful control of the reaction conditions, e.g. temperature, time, etc., and the addition of pyridine in the gas phase. Haggata et al. further describe the synthesis of nanoparticles in polymer matrices [S. W. Haggata et al., *J. Mater. Chem.*, 1996, 6, 1771; *J. Mater. Chem.*, 1997, 7, 1969]. In a polymeric gas-barrier film, the nucleation and growth of quantum dots from gaseous precursors may proceed in any defects or voids. Since quantum dot stability increases with particle size, under suitable reaction conditions particle growth may continue until all the space is occupied.

Confocal microscopy is an optical imaging technique used to increase optical resolution and contrast of a micrograph by using point illumination and a spatial pinhole to eliminate out-of-focus light in specimens that are thicker than the focal plane. It enables the reconstruction of three-dimensional structures from the obtained images. This technique has gained popularity in the scientific and industrial communities and typical applications are in life sciences, semiconductor inspection and materials science.

The present disclosure relates to the gas-phase synthesis of quantum dots within defects in gas-barrier films, with the film matrix acting as a template for nanoparticle growth. The method may be used to detect the nature and dimensions of defects from the emission characteristics of the quantum dots.

The method described herein may be used to synthesize quantum dots including, but not restricted to, the following materials: Group II-VI nanoparticles, e.g. CdS, CdSe, ZnS, ZnSe, Group III-V nanoparticles, e.g. InP, GaP, Group II-V nanoparticles, e.g. $Cd_3P_2$, and Group III-VI nanoparticles, e.g. $In_2Se_3$.

Suitable gas-phase precursors may include, but are not restricted to, a Group II or Group III cation source, e.g. $R_2Cd/Zn$; $R_3Ga/In$ (R=organic group), and a Group V or Group VI anion source, e.g. $H_2S$, $H_2Se$ or $H_3P$.

The flow rate of the gas-phase precursors may be controlled using a carrier gas. The carrier gas may be an inert gas, e.g. He, $N_2$ or Ar, or a reducing gas, e.g. $H_2$, but is not restricted to these.

Suitable gas-barrier materials, acting as a template for nanoparticle growth, may include, but are not restricted to, polymer matrices, including acrylates, epoxides, polyamides, polyimides, polyesters, cellulose derivatives; inorganic matrices such as dielectrics materials, metal oxides, metal nitrides, or silica-based (glass) materials; and inorganic-organic hybrids including silica-acetate hybrids, hydrosilated polybutadiene and derivatives thereof.

The reaction may optionally be carried out in the presence of a Lewis base in the gas phase to control the nanoparticle growth. Suitable Lewis bases include, but are not restricted to, pyridine gas. The gas-barrier film matrix may comprise a polymeric material that may act as a Lewis base.

Figure 2A:
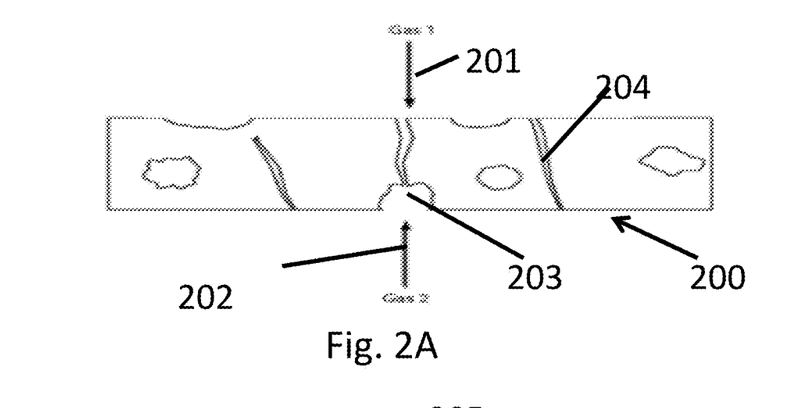
FIGS. 2A and 2B are a diagram showing the detection of full-thickness defects in a gas-barrier film by the formation of quantum dots from gaseous precursors provided with counter current gas streams.

In one embodiment, a gas-barrier film 200 is placed in the middle of two streams of gas flowing from opposite directions, 201 and 202, respectively, as illustrated in FIG. 2A. By placing a gas-barrier film in the middle of two gas streams, the presence of any full-thickness pores 203 or channels 204 allow the gases to diffuse through the film, and nanoparticle nucleation and growth may ensue in pinholes and/or cracks.

Figure 2B:
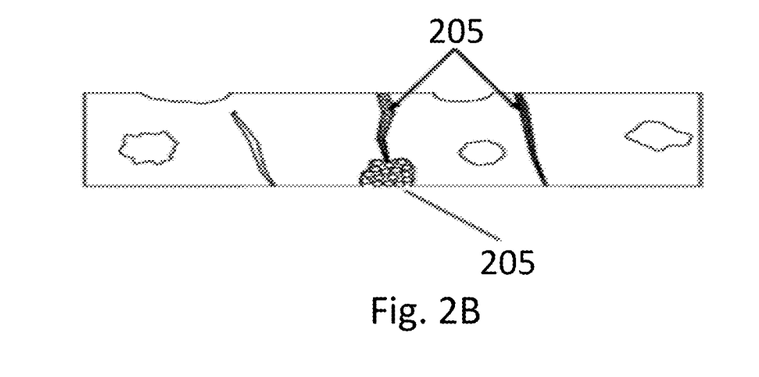

The size of the nanoparticles 205 is restricted by the pore/crack diameter. Small changes in defect diameter and the concurrent change in particle size may is observed visually as a change in the photoluminescence wavelength ($PL_{max}$) under UV light. Correlation of the UV/vis absorption or $PL_{max}$ with particle size is used to determine the pore/crack diameter. Using confocal microscopy, the size and nature of pores is then be determined. Using this experimental configuration, defects directly compromising the film integrity are detected.

Figure 3A:
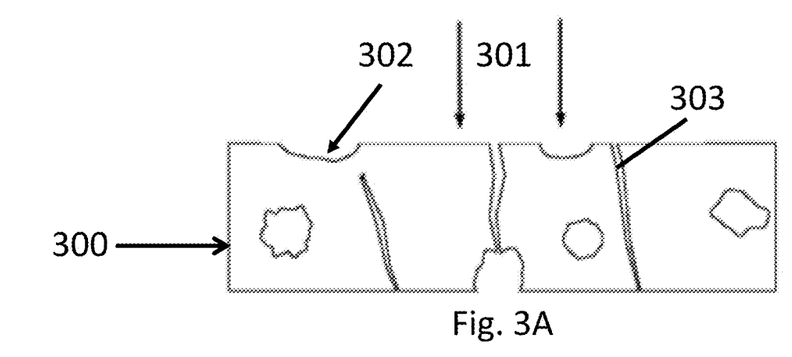
FIGS. 3A and 3B are a diagram showing the detection of surface and full-thickness defects in a gas-barrier film by the formation of quantum dots from gaseous precursors provided with parallel gas streams.
Figure 3B:
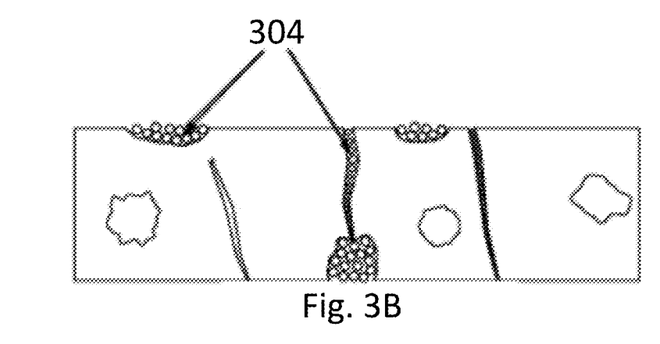

In another embodiment, a gas-barrier film 300 is placed in the stream 301 of two parallel gas sources, as illustrated in FIG. 3A. The gas streams are allowed to flow either sequentially or in tandem. By placing a gas-barrier film in the flow of two parallel gas streams, the gaseous precursors diffuse into any defects in contact with the surface and react, allowing nanoparticle nucleation and growth to proceed in any surface pores 302 or cracks 303 not necessarily penetrating the full thickness of the film. As illustrated in FIG. 3B, the size of the resultant nanoparticles 304 is restricted by the defect diameter, thus, small changes in defect diameter result in changes in the particle size that may be observed visually as a change in the photoluminescence wavelength ($PL_{max}$) under UV irradiation. Correlation of the UV/vis absorption maximum or $PL_{max}$ with particle size may be used to determine the pore/crack diameter. Using confocal microscopy, the size and nature of pores may then be determined. Using this experimental configuration, defects compromising the film integrity, along with those with potential to propagate the full-thickness of the film, may be detected.

Figure 4:
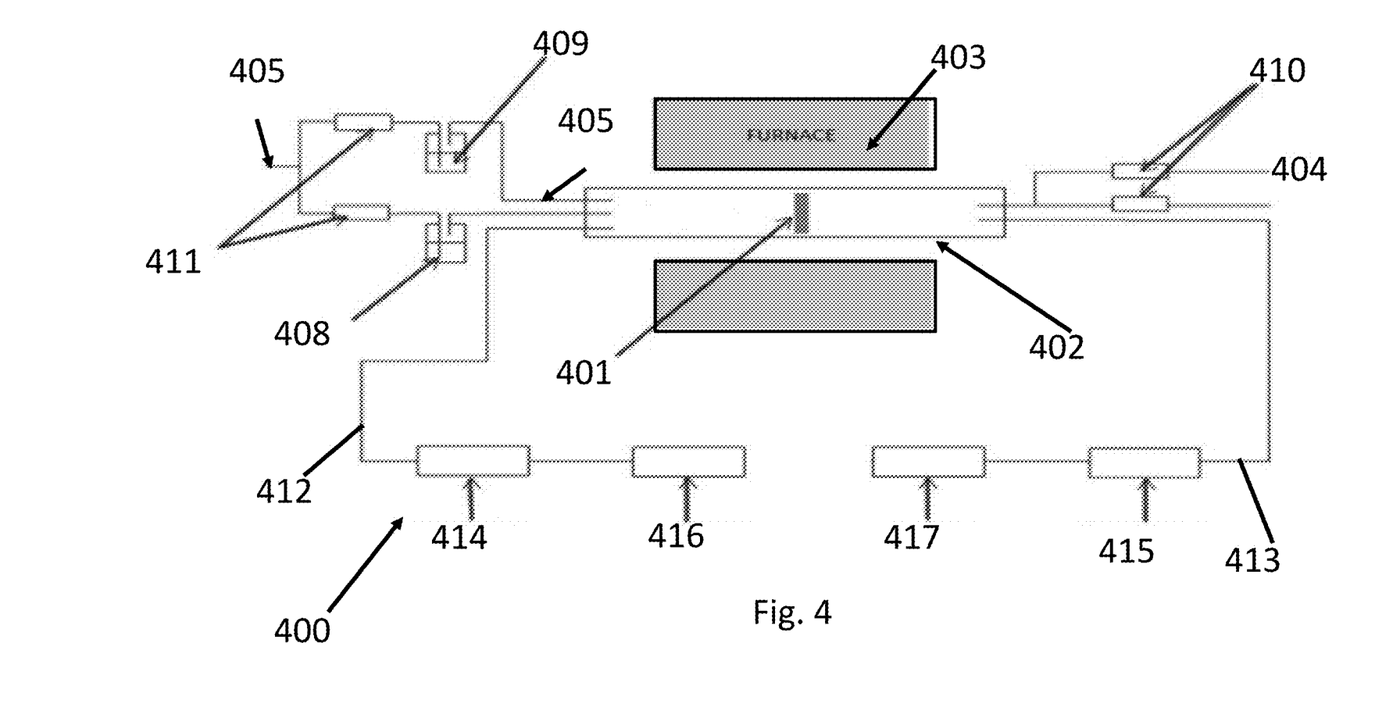
FIG. 4 illustrates an apparatus for providing counter-current flow of QD precursor gases.
Figure 5:
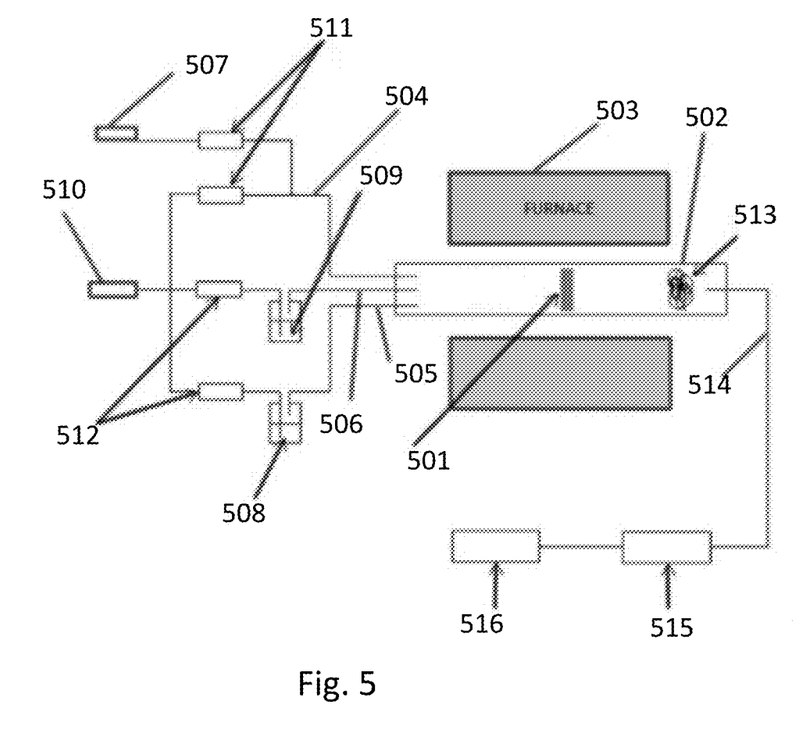
FIG. 5 illustrates an apparatus for providing parallel flow of QD precursor gases.

FIGS. 4 and 5 illustrate apparatuses for the gas-phase synthesis of quantum dots. In the apparatus 400 illustrated in FIG. 4A a gas-barrier film 401 is inserted into a quartz tube 402, which is then positioned in a tube furnace 403. QD precursor gasses are provided by lines 404 and 405 to opposite sides of the gas barrier film. For example, line 404 may provide a gas phase QD precursor such as $H_2S$, $H_2Se$, or $PH_3$ and line 405 may provide a QD precursor such as $R_2Zn$, $R_2Cd$, $R_3Ga$ or $R_3In$. Apparatus 400 can also include lines 406 and 407 for carrier gasses. Apparatus 400 may also include a source 408 for providing a Lewis base. Precursor gas lines may include a reactor 409 for generating gaseous precursors. Any or all of the gas lines may be provided with gas-flow meters 410 and 411. Exhaust lines 412 and 413 may be provided with scrubbers 414 and 415, respectively, and with pressure controllers 416 and 417 respectively.

In the apparatus 500 illustrated in FIG. 5, gas barrier film 501 is positioned into a quartz tube 502, which is positioned in tube furnace 503. The gas barrier film is exposed to parallel streams of QD precursor gas provided by lines 504 and 505. The apparatus may also include one or more lines 506 providing additional reagents, such as a Lewis base. Lines 504 and 505 are connected to sources of QD precursor gasses 507 and 508, respectively. In apparatus 500, line 506 can be connected to a source of Lewis base 509. As in the apparatus illustrated in FIG. 4, example precursor gasses for apparatus 500 include $H_2S$, $H_2Se$, or $PH_3$ and $R_2Zn$, $R_2Cd$, $R_3Ga$ or $R_3In$. Any of the gas lines can also be provided with a source of carrier gas 510 and additional equipment, such as gas-flow meters 511 and 512. Quartz tube 502 may contain glass wool 513 up stream of exhaust line 514. Exhaust line 514 may be equipped with monitoring, control, or processing equipment, such as one or more scrubbers 515 and pressure controller 516.

The particular set-ups illustrated in FIGS. 4 and 5 are exemplary and schematic only. It will be readily apparent to one of skill in the art how to implement these and other geometries for providing QD precursor gasses to a gas barrier film, as described herein. The scope of the invention is not limited to any particular reactor geometry or apparatus.

Figure 6:
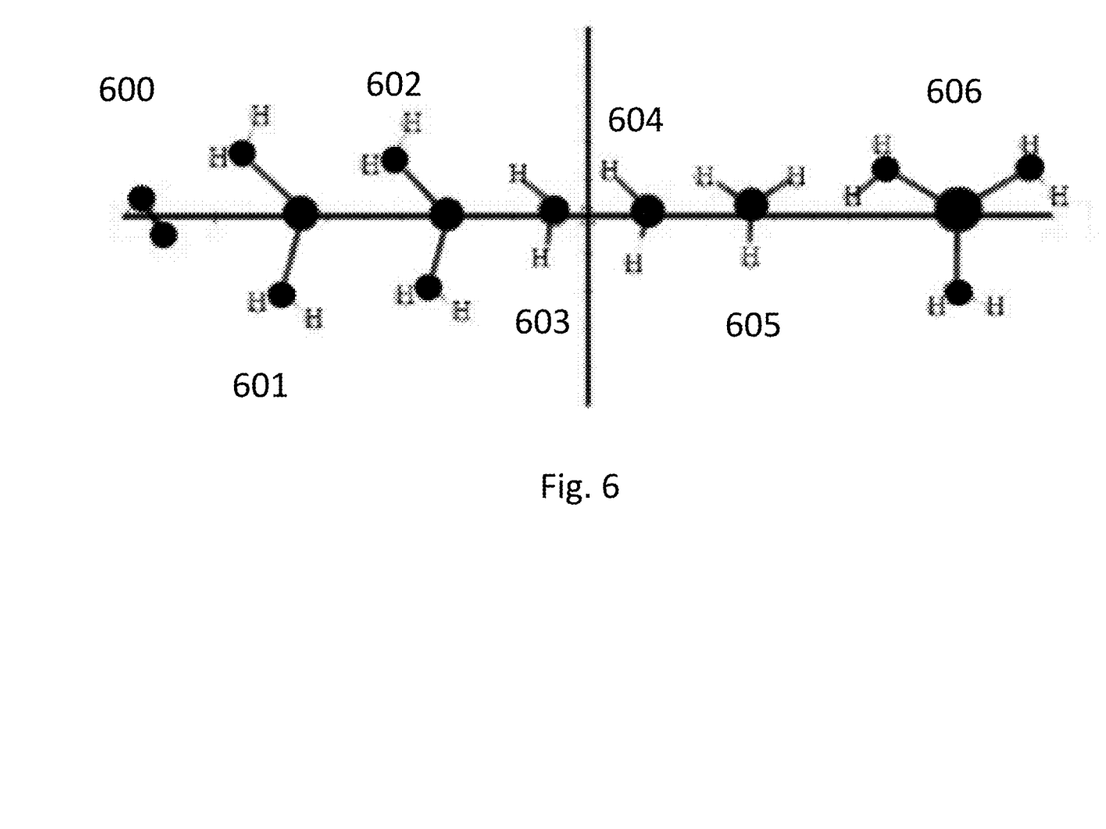
FIG. 6 is a diagram comparing the relative size of an oxygen molecule to gas-phase precursor molecules of quantum dots.

The methods described herein are capable of detecting fine defects in gas barrier films because the gas phase QD precursors can diffuse into small-diameter defects and react inside those defects. FIG. 6 compares the relative size of QD precursor molecules $Me_2Cd$ 601, $Me_2Zn$ 602, $H_2S$ 603, $H_2Se$ 604, $PH_3$ 605, and $InMe_3$ 606 to the size of $O_2$ 600.

Figure 7:
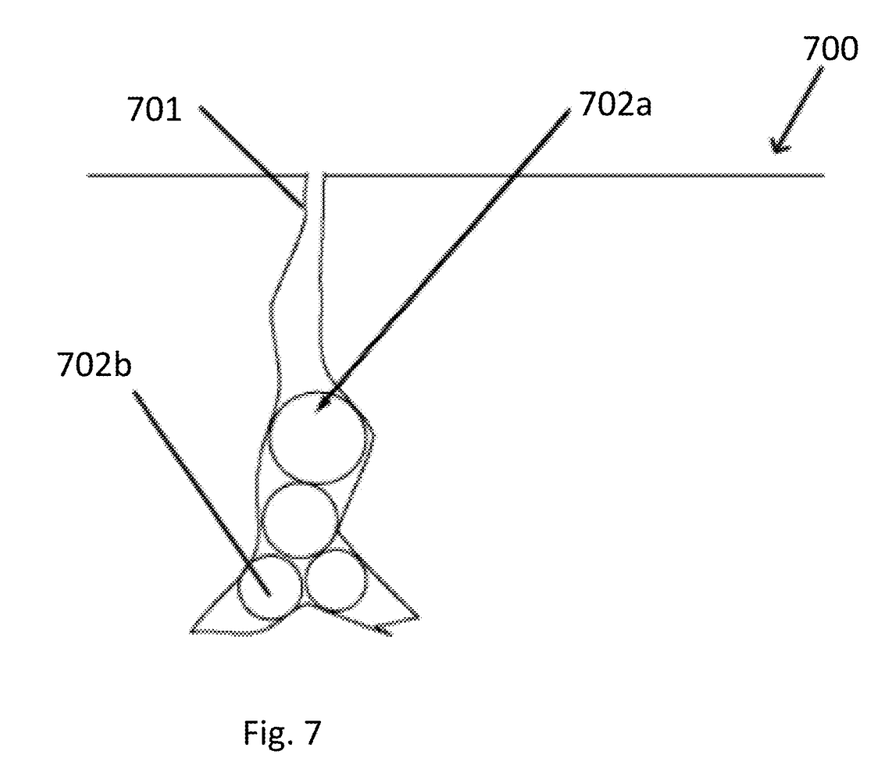
FIG. 7 illustrates the formation of quantum dots within a bottle-neck shaped pore in a gas-barrier film.

FIG. 7 illustrates the formation of quantum dots within a bottle-neck shaped pore 701 in a gas-barrier film 700. Gaseous QD precursors can diffuse into pores and cracks in the gas-barrier film that are as small as 1 nm in width or less. The QD precursors react within the pores to form QDs 702. In wide portions of the cracks the precursors react to form large diameter QDs 702a. In narrower portions of cracks only smaller diameter QDs 702b can form. Since the larger QDs emit light that is red-shifted compared to the smaller QDs, the color of the emission of the QDs in the cracks provides an indication of the defect structure in the film.

EXAMPLES

Example 1

CdS

CdS quantum dots may be formed from the gas phase reaction of helium gas streams containing $Me_2Cd$ and $H_2S$ in the presence of pyridine gas. Typical reaction conditions include a He flow rate of ~600 cm$^3$ min$^{-1}$ and a 30-fold excess of $H_2S$ to $Me_2Cd$. The particle size may be controlled by varying the pyridine concentration and/or the reaction temperature. Preferably, pyridine:$Me_2Cd$ ratios in the range 1:20 to 2:1, and temperatures between room temperature and 200° C. are employed. It has been found that increasing the pyridine concentration reduces the particle size, while the particle size increases with increasing temperature.

The absorption of the CdS nanoparticles may be tuned from the UV to cyan (bulk band gap ~512 nm) depending on the particle size. For example, nanoparticles in the size range 2-20 nm may be expected to emit between approximately 320-500 nm, corresponding with UV to cyan light.

Example 2

CdSe

Reaction conditions similar to those outlined for CdS (above) may be used to synthesize CdSe quantum dots [N. L. Pickett et al., *J. Mater. Chem.*, 1997, 7, 1855], substituting $H_2S$ for $H_2Se$. Higher pyridine concentrations may be used to control the particle size (up to 150:1 pyridine:$Me_2Cd$).

The absorption of the CdSe nanoparticles may be tuned from the blue to the deep red (bulk band gap ~717 nm) depending on the particle size. Nanoparticles in the size range 2-20 nm may be expected to emit between approximately 490-700 nm, corresponding with blue to deep red light.

Example 3

ZnS

Reaction conditions similar to those outlined for CdS (above) may be used to synthesize ZnS quantum dots [N. L.

Pickett et al., *J. Mater. Chem.*, 1997, 7, 1855], substituting Me$_2$Cd for Me$_2$Zn. Higher reaction temperatures (up to 300° C.) may be advantageous.

The absorption of the ZnS nanoparticles may be tuned across the UV spectrum (bulk band gap ~344 nm) depending on the particle size. Nanoparticles in the size range 2-20 nm may be expected to emit between approximately 235-340 nm.

Example 4

ZnSe

Reaction conditions similar to those outlined for ZnS (above) may be used to synthesize ZnSe quantum dots [N. L. Pickett et al., *J. Mater. Chem.*, 1997, 7, 1855], substituting H$_2$S for H$_2$Se. A reducing H$_2$ carrier gas, rather than inert He, may be more effective at controlling the particle size.

The absorption of the ZnS nanoparticles may be tuned from the UV to the blue (bulk band gap ~459 nm) depending on the particle size. Nanoparticles in the size range 2-20 nm may be expected to emit between approximately 295-455 nm, corresponding with UV to indigo light.

Example 5

InP

InP nanoparticles may be synthesized using a reaction procedure similar to those outlined for II-VI quantum dots (above) from Me$_3$In and PH$_3$ gaseous precursors.

The absorption of the InP nanoparticles may be tuned from the green to the near-IR (bulk band gap ~925 nm) depending on the particle size. Nanoparticles in the size range 2-20 nm may be expected to emit between approximately 520-875 nm, corresponding with green light to IR radiation.

Following the treatment to synthesize quantum dots within the defects in a gas-barrier film, the particle size may be studied by confocal microscopy. Confocal microscopy may be used to detect the fluorescence over very small areas, typically around 200 nm×200 nm for confocal laser scanning microscopy, but even down to below 10 nm×10 nm using stimulated emission depletion microscopy. Analysis of the film by this technique allows the defect structure to be mapped out visually, with areas of fluorescence corresponding to cracks or pores. Further, by de-convoluting the fluorescence wavelength at specific locations within the film, the corresponding particle size may be estimated, giving an indication of the defect diameter.

To effectively detect defects in gas-barrier films, the method must be sufficiently sensitive such that the level of detection is comparable to the size of the gas molecules that the film aims to impede. It is also useful to be able to examine the nature and structure of a defect, without assuming a particular defect geometry. The technique should not be destructive to the film, since this may create artefacts or cause crack propagation, which may reduce the validity of the analysis.

The methods described to detect defects in gas-barrier films in the prior art fail to encompass all of the essential criteria. The present method uses gaseous precursors, which though larger than individual oxygen and water molecules, are of the same order of magnitude. As illustrated in FIG. 6, the gaseous precursors suggested herein are less than three times the length of an oxygen molecule (~3 Å) along their longest axis, which enables them to diffuse into defects less than 1 nm in diameter, i.e. below the lower limit for quantum dot stability. As shown in FIG. 7, if this crack subsequently widens to a size that corresponds to a diameter within the stable quantum dot range, nanoparticle formation may proceed and may be detected reliably and accurately. Using prior art techniques such as high pressure nitrogen adsorption, wherein the detection limit may be smaller than that of the present invention, the results become unreliable towards the detection limit. In contrast, the method of the present invention provides reliable results across that entire detection range. Further, in utilizing gaseous precursors, the technique effectively examines the penetrability of a film to gaseous molecules, thus testing its primary function. This is in contrast to liquid-phase detection methods, wherein the wettability of the liquid on the solid film may influence the results.

Using the method of the present invention, cryogenic temperatures, which may be damaging to gas-barrier films and may be challenging and costly to maintain, are not required. Moreover, the film need not be exposed to potentially-damaging high pressures. Consequently, the detection method does not introduce new artifact-type defects into the film during characterisation. Since the nanoparticle size may be controlled by a number of parameters, including temperature, time, carrier gas, and the concentration of optional Lewis base, the technique may be adapted for use with a wide range of gas-barriers. Neither is the technique specific to the detection of a particular defect conformation, unlike nitrogen adsorption that assumes and relies upon a cylindrical pore shape.

Since QDs fluoresce with different emission wavelengths depending on the particle size, de-convolution of fluorescence measurements in conjunction with confocal microscopy may be used to provide a visual representation of the defect structure within the film. This visual information may provide a comprehensive representation of the nature and distribution of defects, as well as insight into the potential for crack propagation. Overall the present invention may be used to provide a thorough depiction of the structure of a gas-barrier film and consequently the potential effect of defects on the integrity and efficacy of that film.

Although particular embodiments of the present invention have been shown and described, they are not intended to limit what this patent covers. One skilled in the art will understand that various changes and modifications may be made without departing from the scope of the present invention as literally and equivalently covered by the following claims.

What is claimed is:

1. A method for characterizing defects in a gas-barrier film comprising:
    synthesizing quantum dots within defects in the film using gaseous precursors;
    detecting light emission or light absorbance by the quantum dots.

2. A method as recited in claim 1 wherein the defects comprise channel cracks in the film.

3. A method as recited in claim 1 wherein the defects comprise open pores in the film.

4. A method as recited in claim 1 wherein the fluorescence is detected using confocal microscopy.

5. A method as recited in claim 1 wherein the quantum dots comprise Group II-VI nanoparticles.

6. A method as recited in claim 1 wherein the quantum dots comprise Group III-V nanoparticles.

7. A method as recited in claim 1 wherein the quantum dots comprise Group II-V nanoparticles.

8. A method as recited in claim 1 wherein the quantum dots comprise Group III-VI nanoparticles.

9. A method as recited in claim 1 wherein the gaseous precursors are supplied via a carrier gas selected from the group consisting of helium (He), nitrogen ($N_2$), argon (Ar) and hydrogen ($H_2$).

10. A method as recited in claim 1 wherein the quantum dots are synthesized in the presence of a Lewis base.

11. A method as recited in claim 10 wherein the Lewis base is pyridine gas.

12. A method as recited in claim 1 wherein the gaseous precursors comprise two streams flowing in opposite directions.

13. A method as recited in claim 1 wherein the gaseous precursors comprise two streams flowing in parallel.

14. A method as recited in claim 13 wherein the two streams flow in tandem.

15. A method as recited in claim 13 wherein the two streams flow sequentially.

16. A method as recited in claim 1 wherein the quantum dots comprise nanoparticles selected from the group consisting of CdS, CdSe, ZnS, ZnSe and InP.

17. A method as recited in claim 1 wherein the fluorescence is detected by stimulated emission depletion microscopy.

18. A method as recited in claim 1 further comprising correlating the photoluminescence wavelength of the quantum dots with their particle size.

19. A method as recited in claim 1 further comprising determining the size of pores in the film using confocal microscopy.

20. A method as recited in claim 1 further comprising correlating the absorption wavelengths of the quantum dots to particle size determined by transmission electron microscopy.

21. A method as recited in claim 1 further comprising correlating the emission wavelengths of the quantum dots to particle size determined by transmission electron microscopy.

* * * * *